(12) United States Patent
Kariyazono et al.

(10) Patent No.: US 9,273,185 B2
(45) Date of Patent: Mar. 1, 2016

(54) EPISULFIDE COMPOUND AND OPTICAL MATERIAL COMPOSITION

(71) Applicant: MITSUBISHI GAS CHEMICAL COMPANY, INC., Tokyo (JP)

(72) Inventors: Kazuki Kariyazono, Osaka (JP); Takashi Aoki, Osaka (JP); Hiroyuki Okada, Osaka (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/439,061

(22) PCT Filed: Mar. 12, 2014

(86) PCT No.: PCT/JP2014/056397
§ 371 (c)(1),
(2) Date: Apr. 28, 2015

(87) PCT Pub. No.: WO2014/142138
PCT Pub. Date: Sep. 18, 2014

(65) Prior Publication Data
US 2015/0259477 A1    Sep. 17, 2015

(30) Foreign Application Priority Data

Mar. 14, 2013 (JP) ................. 2013-052124

(51) Int. Cl.
C08G 75/00 (2006.01)
C08G 75/08 (2006.01)
C07D 331/02 (2006.01)

(52) U.S. Cl.
CPC .............. *C08G 75/08* (2013.01); *C07D 331/02* (2013.01)

(58) Field of Classification Search
CPC .......... C08G 75/08; G02B 1/04; C08L 81/00; B29B 13/00; B30B 9/28
USPC ....................................... 528/375
See application file for complete search history.

(56) References Cited

U.S. PATENT DOCUMENTS

| 6,117,923 | A  | 9/2000  | Amagi et al.   |
|-----------|----|---------|----------------|
| 6,472,495 | B1 | 10/2002 | Yoshimura et al.|
| 2003/0171533 | A1 | 9/2003 | Tamura et al. |
| 2005/0261467 | A1 | 11/2005 | Tamura et al.|

FOREIGN PATENT DOCUMENTS

| EP | 1046931 A2 | 10/2000 |
| EP | 2058346 A1 | 5/2009 |
| EP | 2243798 A1 | 10/2010 |
| JP | H09-110979 | 4/1997 |
| JP | H10-298287 | 11/1998 |
| JP | 2000-327677 | 11/2000 |
| JP | 2001-002783 | 1/2001 |
| JP | 2001-131257 | 5/2001 |
| JP | 2002-122701 | 4/2002 |
| JP | 2004-027203 | 1/2004 |
| JP | 2005-272418 | 10/2005 |
| JP | 2007-321072 | 12/2007 |
| WO | 02/083763 | 10/2002 |
| WO | 2012/147710 | 11/2012 |

OTHER PUBLICATIONS

International Search Report issued in PCT/JP2014/056397 on Jun. 3, 2014 and English language version thereof.
Written Opinion issued in PCT/JP2014/056397 on Jun. 3, 2014 and partial English language translation thereof.
Search Report issued by European patent office in Patent Application No. 14763924.9, dated Sep. 15, 2015.
Search Report issued by Chinese patent office in Patent Application No. 201480002905.0 dated Oct. 10, 2015.

*Primary Examiner* — Shane Fang
(74) *Attorney, Agent, or Firm* — Greenblum & Bernstein, P.L.C.

(57) ABSTRACT

According to a preferred embodiment of the present invention, with an optical material compound including an episulfide compound represented by formula (1) and an episulfide compound represented by formula (2), it is possible to stably and inexpensively store the episulfide compound represented by formula (2) and also provide an optical material having excellent light resistance (in formula (1), m represents an integer from 0 to 4, and n represents an integer from 0 to 2) (in formula (2), m represents an integer from 0 to 4, and n represents an integer from 0 to 2).

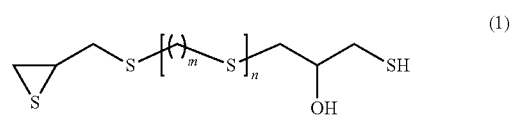

(1)

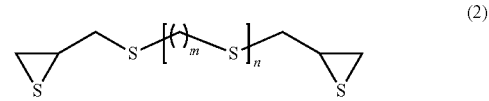

(2)

10 Claims, No Drawings

EPISULFIDE COMPOUND AND OPTICAL MATERIAL COMPOSITION

TECHNICAL FIELD

The present invention relates to an episulfide compound, which is preferably usable for optical materials such as plastic lenses, prisms, optical fibers, information storage discs, filters or the like, especially for plastic lenses.

BACKGROUND ART

A plastic lens is lightweight, highly tough and easy to be dyed. Properties required of a plastic lens are low specific gravity, high transparency, and low yellow index. Optical properties required of a plastic lens are high refractive index, high Abbe number, high heat resistance, and high strength. A high refractive index allows the lens to be thinner, and a high Abbe number decreases the chromatic aberration of the lens.

Recently, many organic compounds containing sulfur atoms produced for the purpose of providing a high refractive index and a high Abbe number have been reported. Among these compounds, polyepisulfide compounds containing sulfur atoms are known to provide a good balance of the refractive index and the Abbe number (Patent Document 1). Since polyepisulfide compounds are reactive with various types of compounds, compositions of polyepisulfide compounds and various types of compounds have been proposed for the purpose of enhancing the properties (Patent Documents 2 through 5).

However, episulfide compounds, which are highly reactive, are difficult to be stored for a long time. A technique of storing episulfide compounds in a refrigerated state (Patent Document 6) and a technique of adding an epoxy compound containing a halogen group (Patent Document 7) have been proposed.

PRIOR ART DOCUMENTS

Patent Documents

Patent Document 1: Japanese Laid-Open Patent Publication No. H09-110979
Patent Document 2: Japanese Laid-Open Patent Publication No. H10-298287
Patent Document 3: Japanese Laid-Open Patent Publication No. 2001-002783
Patent Document 4: Japanese Laid-Open Patent Publication No. 2001-131257
Patent Document 5: Japanese Laid-Open Patent Publication No. 2002-122701
Patent Document 6: Japanese Laid-Open Patent Publication No. 2000-327677
Patent Document 7: Japanese Laid-Open Patent Publication No. 2005-272418

SUMMARY OF THE INVENTION

Problems to be Solved by the Invention

However, storage in a refrigerated state requires a dedicated refrigeration device and thus is costly, and an epoxy compound containing a halogen group lowers the light resistance due to halogen. For these reasons, improvement has been desired.

The present invention has an object of providing a composition for an optical material which allows a polymerizable compound such as an episulfide compound or the like to be stably and at low cost, and also provides a highly light-resistant optical material.

Means for Solving the Problems

In light of such a situation, the present inventors accumulated active studies and found that the above-described object can be achieved by the present invention described below. The present invention is as follows.

<1> An episulfide compound represented by formula (1) below:

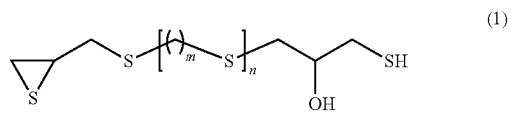

(where m represents an integer of 0 to 4, and n represents an integer of 0 to 2).

<2> A composition for an optical material, comprising the episulfide compound according to <1>, and a polymerizable compound.

<3> The composition for an optical material according to <2>, wherein the episulfide compound is contained at a content of 0.001 to 5.0% by mass.

<4> The composition for an optical material according to <2> or <3>, wherein the polymerizable compound is contained at a content of 95.0 to 99.999% by mass.

<5> The composition for an optical material according to any one of <2> through <4>, wherein an episulfide compound represented by formula (2) below is contained as the polymerizable compound:

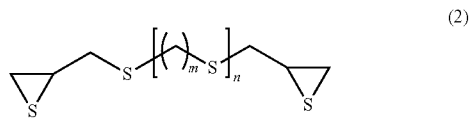

(where m represents an integer of 0 to 4, and n represents an integer of 0 to 2).

<6> The composition for an optical material according to <5>, wherein the episulfide compound represented by formula (2) is contained at a content of 40 to 99.999% by mass.

<7> A method for producing an optical material, comprising adding a polymerization catalyst to the composition for an optical material according to any one of <2> through <6> at a content of 0.0001% by mass to 10% by mass with respect to the total amount of the composition for an optical material, thereby causing polymerization and curing.

<8> An optical material produced by the method according to <7>.

<9> An optical lens, comprising the optical material according to <8>.

<10> A method for producing the episulfide compound represented by formula (1) below according to <1>:

(where m represents an integer of 0 to 4, and n represents an integer of 0 to 2),
the method comprising the steps of:
reacting hydrogen sulfide or a polythiol compound with an epihalohydrin compound to obtain a compound represented by formula (3) below;
reacting the obtained compound represented by formula (3) with an alkali to proceed with a dehydrohalogenation reaction to obtain a compound represented by formula (4) below; and
reacting the obtained compound represented by formula (4) with a thiating agent to obtain the compound represented by formula (1) above:

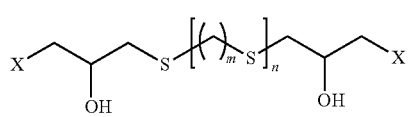

(where X represents a halogen atom, m represents an integer of 0 to 4, and n represents an integer of 0 to 2);

(where X represents a halogen atom, m represents an integer of 0 to 4, and n represents an integer of 0 to 2).

Advantageous Effect of the Invention

According to the present invention, a composition for an optical material is provided which allows a polymerizable compound such as an episulfide compound or the like, used to produce an optical material having a high refractive index, to be stored stably and at low cost, and also provides a highly light-resistant optical material.

EMBODIMENTS FOR CARRYING OUT THE INVENTION

Hereinafter, the present invention will be described in detail.

An embodiment according to the present invention relates to an episulfide compound represented by formula (1) shown above, and another embodiment according to the present invention relates to a composition for an optical material including the episulfide compound represented by formula (1) and a polymerizable compound. Examples of the polymerizable compound include episulfide compounds, vinyl compounds, methacrylic compounds, acrylic compounds, allyl compounds and the like. Episulfide compounds are preferable, and episulfide compounds represented by formula (2) shown above are more preferable.

An episulfide compound represented by formula (1) is contained in a composition for an optical material according to the present invention preferably at a content of 0.001 to 5% by mass, more preferably at a content of 0.005 to 3.0% by mass, and especially preferably at a content of 0.01 to 1.0% by mass. When the content of the episulfide compound represented by formula (1) is less than 0.001% by mass, a sufficient effect may not be provided. When the content of the episulfide compound represented by formula (1) exceeds 5.0% by mass, the heat resistance may be decreased. A polymerizable compound is contained in the composition for an optical material according to the present invention preferably at a content of 95.0 to 99.999% by mass, more preferably at a content of 97.0 to 99.995% by mass, and especially preferably at a content of 99.0 to 99.99% by mass. In the case where an episulfide compound represented by formula (2) is used as the polymerizable compound, the episulfide compound represented by formula (2) is contained in the composition for an optical material preferably at a content of 40 to 99.999% by mass, more preferably at a content of 50 to 99.995% by mass, and especially preferably at a content of 60 to 99.99% by mass.

Hereinafter, an episulfide compound represented by formula (1) and an episulfide compound represented by formula (2) will be described in detail.

An embodiment according to the present invention relates to an episulfide compound represented by formula (1) shown above. The episulfide compound represented by formula (1) is used for a composition for an optical material, to which another embodiment according to the present invention relates. Regarding a compound represented by formula (1), it is preferable that m is an integer of 0 to 2 and n is an integer of 0 or 1; it is more preferable that m is 0 and n is 1, or that n is 0; it is mostly preferable that n is 0. Episulfide compounds represented by formula (1) may be used independently or as a mixture of two or more thereof.

Specific examples of the episulfide compound represented by formula (1) include 1-mercapto-2-hydroxy-6,7-epithio-4-thiaheptane, 1-mercapto-2-hydroxy-7,8-epithio-4,5-dithiaoctane, 1-mercapto-2-hydroxy-8,9-epithio-4,6-dithianonane, 1-mercapto-2-hydroxy-9,10-epithio-4,7-dithiadecane, 1-mercapto-2-hydroxy-12,13-epithio-4,7,10-trithiatridecane, and the like. Among these, 1-mercapto-2-hydroxy-6,7-epithio-4-thiaheptane and 1-mercapto-2-hydroxy-7,8-epithio-4,5-dithiaoctane are preferable.

Hereinafter, a method for producing an episulfide compound represented by formula (1) according to the present invention will be described. The production method is not limited to the following.

A method for producing an episulfide compound represented by formula (1) according to the present invention is as follows. Hydrogen sulfide or a polythiol compound and an epihalohydrin compound are reacted to obtain a compound represented by formula (3) shown below. Next, the obtained compound represented by formula (3) is reacted with an alkali to proceed with a dehydrohalogenation reaction to obtain a compound represented by formula (4) shown below. Then, the obtained compound represented by formula (4) is reacted with a thiating agent such as thiourea, thiocyanate or the like to obtain an episulfide compound represented by formula (1).

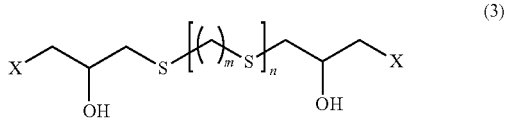

(3)

(In the formula, X is a halogen atom, m is an integer of 0 to 4, and n is an integer of 0 to 2).

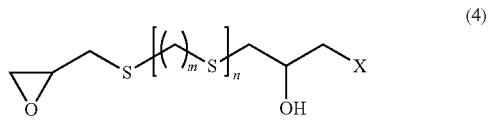

(4)

(In the formula, X is a halogen atom, m is an integer of 0 to 4, and n is an integer of 0 to 2).

A method for producing the compound represented by formula (3) will be described.

The compound represented by formula (3) is obtained by a reaction of hydrogen sulfide or a polythiol compound and an epihalohydrin compound. Example of the polythiol compound include methanediol, 1,2-dimercaptoethane, 1,3-dimercaptopropane, 1,4-dimercaptobutane, bis(2-mercaptoethyl)sulfide, and the like. Among hydrogen sulfide and the polythiol compounds, hydrogen sulfide, 1,2-dimercaptoethane, and bis(2-mercaptoethyl)sulfide are preferable. Hydrogen sulfide is most preferable. Examples of the epihalohydrin compound include epichlorohydrin and epibromohydrin, and the like. Epichlorohydrin is preferable.

For reacting epihalohydrin and hydrogen sulfide or a polythiol compound, it is preferable to use a catalyst. Examples of the catalyst include inorganic acid, organic acid, Lewis acid, silicic acid, boric acid, quaternary ammonium salt, inorganic base, organic salt, and the like. Organic acid, quaternary ammonium salt, and inorganic base are preferable. Quaternary ammonium salt and inorganic base are more preferable. Specific examples thereof include tetramethylammoniumchloride, tetramethylammoniumbromide, tetramethylammoniumacetate, tetraethylammoniumchloride, tetraethylammoniumbromide, tetraethylammoniumacetate, tetrabutylammoniumchloride, tetrabutylammoniumbromide, tetraoctylammoniumacetate, tetrahexylammoniumchloride, tetrahexylammoniumbromide, tetrahexylammoniumacetate, tetraoctylammoniumchloride, tetraoctylammoniumbromide, tetraoctylammoniumacetate, sodium hydroxide, potassium hydroxide, magnesium hydroxide, calcium hydroxide, and the like. Among these, sodium hydroxide, potassium hydroxide, and calcium hydroxide are preferable.

There is no specific limitation on the amount of the catalyst as long as the reaction proceeds properly. The amount of the catalyst with respect to 1 mol of epihalohydrin is preferably 0.00001 to 0.5 mol, and more preferably 0.001 to 0.1 mol. When the amount of the catalyst is less than 0.00001 mol, the reaction does not proceed or is too slow, which is not preferable. When the amount of the catalyst exceeds 0.5 mol, the reaction proceeds too fast to control, which is not preferable, either.

There is no specific limitation on the ratio of epihalohydrin and hydrogen sulfide or a polythiol compound as long as the reaction proceeds properly. The molar ratio of epihalohydrin with respect to a thiol group (SH group) of the polythiol compound or H of hydrogen sulfide is preferably 0.3 to 4, more preferably 0.4 to 3, and still more preferably 0.5 to 2. When the ratio is less than 0.3 or exceeds 4, excessive amounts of the materials are left unreacted, which is not economically preferable.

It is not necessary to use a solvent. In the case where a solvent is used, any of water, alcohols, ethers, ketones, aromatic hydrocarbons, and halogenated hydrocarbons is usable. Specific examples thereof include water, methanol, ethanol, propanol, isopropanol, diethylether, tetrahydrofuran, dioxane, methylcellosolve, ethylcellosolve, butylcellosolve, methylethylketone, acetone, benzene, toluene, xylene, dichloroethane, chloroform, chlorobenzene, and the like. Among these, water, methanol, and toluene are preferable. Water and methanol are most preferable.

There is no specific limitation on the reaction temperature as long as the reaction proceeds properly. The reaction temperature is preferably −10° C. to 80° C., more preferably 0° C. to 50° C., and still more preferably 0° C. to 40° C. There is no specific limitation on the reaction time. The reaction time is usually 20 hours or shorter. When the reaction temperature is lower than −10° C., the reaction does not proceed or is too slow, which is not preferable. When the reaction temperature exceeds 80° C., the reaction product is turned into oligomer and has a high molecular weight, which is not preferable.

A compound represented by formula (3) and having a disulfide bond with m=0 and n=1 may be obtained as follows. Epihalohydrin and hydrogen sulfide are reacted to obtain a compound containing halogeno group, alcoholic hydroxyl group, and thiol group (SH group), and then the SH groups are subjected to an intermolecular reaction by use of a halogen compound and a basic compound and thus are turned into disulfide. Specific examples of the halogen compound usable for turning SH groups into disulfide include chlorine, bromine, and iodine. Bromine and iodine are preferable. The amount of the halogen compound used with respect to 1 mol of SH group is 0.1 to 5 mol, preferably 0.2 to 3 mol, and more preferably 0.3 to 1 mol. When the amount is less than 0.1 mol or exceeds 5 mol, excessive amounts of the materials are left unreacted, which is not economically preferable.

Specific examples of the basic compound include sodium carbonate, potassium carbonate, magnesium carbonate, calcium carbonate, sodium hydrogen carbonate, potassium hydrogen carbonate, sodium hydroxide, potassium hydroxide, magnesium hydroxide, calcium hydroxide, and the like. Sodium carbonate, potassium carbonate, magnesium carbonate, calcium carbonate, sodium hydrogen carbonate, and potassium hydrogen carbonate are preferable.

The amount of the basic compound used with respect to 1 mol of SH group is 0.1 to 10 mol, preferably 0.2 to 5 mol, and more preferably 0.3 to 3 mol. When the amount is less than 0.1 mol or exceeds 10 mol, excessive amounts of the materials are left unreacted, which is not economically preferable.

It is not necessary to use a solvent. In the case where a solvent is used, any of water, alcohols, ethers, ketones, aromatic hydrocarbons, and halogenated hydrocarbons is usable. Specific examples thereof include water, methanol, ethanol, propanol, isopropanol, diethylether, tetrahydrofuran, dioxane, methylcellosolve, ethylcellosolve, butylcellosolve, methylethylketone, acetone, benzene, toluene, xylene, dichloroethane, chloroform, chlorobenzene, and the like. Among these, water, methanol, and toluene are preferable. Water and methanol are most preferable.

There is no specific limitation on the reaction temperature as long as the reaction proceeds properly. The reaction temperature is preferably −10° C. to 80° C., more preferably 0° C. to 50° C., and still more preferably 0° C. to 40° C. There is no specific limitation on the reaction time. The reaction time is usually 20 hours or shorter. When the reaction temperature is lower than −10° C., the reaction does not proceed or is too slow, which is not preferable. When the reaction temperature exceeds 80° C., the reaction product is turned into oligomer and has a high molecular weight, which is not preferable.

A method for producing the compound represented by formula (4) will be described.

The compound represented by formula (4) is obtained by reacting the compound represented by formula (3) with an alkali. Specific examples of the alkali include ammonia, hydroxide of alkaline metal and alkaline earth metal, carbonate of alkaline metal and alkaline earth metal, hydrogencarbonate of alkaline metal, ammonium salt of alkaline metal and alkaline earth metal, and the like. These may be used in the form of an aqueous solution. Sodium hydroxide, potassium hydroxide, calcium hydroxide, sodium carbonate, potassium carbonate, ammonium carbonate, sodium hydrogen carbonate, and potassium hydrogen carbonate are preferable. Sodium hydroxide and potassium hydroxide are more preferable.

The amount of the alkali depends on the compound represented by formula (3) and thus is not uniquely defined. Usually, the amount of the alkali used with respect to the halohydrin equivalent in the compound represented by formula (3) is 0.40 to 0.60 equivalent, preferably 0.42 to 0.57 equivalent, and more preferably 0.45 to 0.55 equivalent. When the amount of the alkali is too small or too large, the yield is decreased.

There is no specific limitation on the type of solvent used for the reaction, and any solvent is usable. Preferably, water, alcohols, ethers, ketones, aliphatic hydrocarbons, aromatic hydrocarbons, and halogenated hydrocarbons are usable. These solvents may be used independently or as a mixture thereof. Specific examples of the alcohols include methanol, ethanol, propanol, isopropanol, and the like. Specific examples of the ethers include diethylether, tetrahydrofuran, dioxane, and the like. Specific examples of the ketones include methylcellosolve, ethylcellosolve, butylcellosolve, methylethylketone, acetone, and the like. Specific examples of the aliphatic hydrocarbons include hexane, heptane, octane, and the like. Specific examples of the aromatic hydrocarbons include benzene, toluene, xylene, and the like. Specific examples of the halogenated hydrocarbons include dichloroethane, chloroform, chlorobenzene, and the like. Water and alcohols are more preferable. Specific examples thereof are water, methanol, propanol, and isopropanol. Among these, water and methanol are preferable.

There is no specific limitation on the amount of the solvent. Usually, the amount of the solvent used with respect to 100 parts by mass of the compound represented by formula (3) is 5 to 1000 parts by mass, preferably 50 to 500 parts by mass, and more preferably 100 to 300 parts by mass.

There is no specific limitation on the reaction temperature as long as the reaction proceeds properly. The reaction temperature is preferably −10° C. to 80° C., more preferably 0° C. to 50° C., and still more preferably 0° C. to 30° C. There is no specific limitation on the reaction time. The reaction time is usually 20 hours or shorter. When the reaction temperature is lower than −10° C., the reaction does not proceed or is too slow, which is not preferable. When the reaction temperature exceeds 80° C., the reaction product is turned into oligomer and has a high molecular weight, which is not preferable.

In more detail, it is preferable to drip the compound represented by formula (3) onto a mixed solvent of an organic solvent and an aqueous solution of a basic compound to cause a reaction. There is no specific limitation on the method for dripping the compound represented by formula (3). The compound may be dripped as it is, may be dripped after being dissolved in a solvent, or without being isolated after being synthesized.

Among the compounds represented by formula (4), a compound with n=0 can be obtained from hydrosulfide metal and epihalohydrin.

Hydrosulfide metal is added to epihalohydrin to cause a reaction. The addition is performed such that the molar ratio of epihalohydrin/hydrosulfide metal is 5 to 20, preferably 5 to 15, and more preferably 5 to 10. The molar ratio herein is not the molar ratio in an actual reaction system, but is a molar ratio between the amount of epihalohydrin initially used for the reaction and the amount of hydrosulfide metal finally incorporated into the mixture.

When the molar ratio of epihalohydrin/hydrosulfide metal is less than 5, a large amount of oligomer is generated and thus the yield may be decreased. By contrast, when the molar ratio of epihalohydrin/hydrosulfide metal exceeds 20, an excessive amount of epihalohydrin is used, which is not economically preferable.

It is preferable that epihalohydrin is added to hydrosulfide metal gradually, instead of at a time, so that the amount of oligomer to be generated is small.

It is not necessary to use a solvent if epihalohydrin and hydrosulfide metal are reacted without a solvent. It is preferable to use a solvent. In the case where a solvent is used, any of water, alcohols, ethers, aliphatic hydrocarbons, aromatic hydrocarbons, and halogenated hydrocarbons is preferably usable. Water and alcohols are more preferable, water and methanol are still more preferable, and methanol is most preferable. These solvents may be used independently or as a mixture thereof It is preferable to use a solvent in order to dissolve hydrosulfide metal. More specifically, it is preferable to react epihalohydrin with hydrosulfide metal dissolved in a solvent. It is more preferable to drip hydrosulfide metal dissolved in a solvent onto epihalohydrin.

The reaction temperature is −5° C. to 30° C., preferably 0° C. to 20° C., and most preferably 5° C. to 15° C. When the reaction temperature is lower than −5° C., the reaction rate is decreased, which is not economically preferable. When the reaction temperature exceeds 30° C., the amount of the episulfide compound represented by formula (2) is increased, which is not preferable.

It is preferable to, after the addition of hydrosulfide metal is finished, stir the substances. The substances are stirred preferably for 1 minute to 10 hours, more preferably for 5 minutes to 5 hours, and still more preferably for 10 minutes to 3 hours.

After the epihalohydrin and hydrosulfide metal start reacting, an alkali may be added to promote the reaction. Specific examples of the alkali include ammonia, hydroxide of alkaline metal and alkaline earth metal, carbonate of alkaline metal and alkaline earth metal, hydrogencarbonate of alkaline metal, ammonium salt of alkaline metal and alkaline earth metal, and the like. These may be used in the form of an aqueous solution. Sodium hydroxide, potassium hydroxide, calcium hydroxide, sodium carbonate, potassium carbonate, ammonium carbonate, sodium hydrogen carbonate, and potassium hydrogen carbonate are preferable. Sodium hydroxide and potassium hydroxide are more preferable.

A method for producing the episulfide compound represented by formula (1) from the compound represented by formula (4) will be described.

The compound represented by formula (4) and a thiating agent such as thiourea, thiocyanate or the like are reacted to obtain the episulfide represented by formula (1). Preferable thiating agents include thiourea, sodium thiocyanate, potassium thiocyanate, and ammonium thiocyanate. Thiourea is especially preferable. The thiating agent is used in a mol corresponding to a sum of epoxy and halogen in the compound represented by formula (4), namely, in a theoretical amount. In the case where the reaction rate or purity is considered important, the thiating agent is used in a mol in the range of the theoretical amount to 2.5 times as large as the theoretical amount, preferably in a mol in the range of 1.3 times as large as the theoretical amount to 2.0 times as large as the theoretical amount, and more preferably in a mol in the range of 1.5 times as large as the theoretical amount to 2.0 times as large as the theoretical amount. There is no specific limitation on the type of solvent as long as the episulfide compound represented by formula (1) and the compound represented by formula (4) are dissolved. Specific examples of the solvent include alcohols such as methanol, ethanol, and the like; ethers such as diethylether, tetrahydrofuran, dioxane, and the like; hydroxyethers such as methylcellosolve, ethylcellosolve, butylcellosolve, and the like; aromatic hydrocarbons such as benzene, toluene, and the like; halogenation hydrocarbons such as dichloroethane, chloroform, chlorobenzene, and the like; water; and the like. Alcohols, aromatic hydrocarbons, and water are preferable. Methanol and toluene are more preferable. These solvents may be used independently or as a mixture thereof.

There is no specific limitation on the reaction temperature as long as the reaction proceeds properly. The reaction temperature is usually 10° C. to 50° C. When the reaction temperature is lower than 10° C., the reaction rate is decreased, and thiourea is not dissolved sufficiently and thus the reaction does not proceed sufficiently. When the reaction temperature exceeds 50° C., generation of a polymer is conspicuous.

It is preferable to add acid, acidic anhydride, or ammonium salt at the time of reaction. Specific examples of the usable acid and acidic anhydride include acidic compounds such as nitric acid, hydrochloric acid, perchloric acid, hypochlorous acid, chlorine dioxide, hydrofluoric acid, sulfuric acid, oleum, sulfuryl chloride, boric acid, arsenic acid, arsenous acid, pyroarsenic acid, phosphoric acid, phosphorous acid, hypophosphorous acid, phosphorus oxychloride, phosphorus oxybromide, phosphorus sulfide, phosphorus trichloride, phosphorus tribromide, phosphorus pentachloride, hydrocyanic acid, chromic acid, dinitrogen pentoxide, sulfur trioxide, boron oxide, arsenic pentoxide, phosphorus pentoxide, chromic anhydride, silica gel, silica alumina, aluminum chloride, zinc chloride, and the like; organic carboxylic acids such as formic acid, acetic acid, peracetic acid, thioacetic acid, oxalic acid, tartaric acid, propionic acid, butyric acid, succinic acid, valeric acid, capronic acid, caprylic acid, naphthenic acid, methylmercaptopropionate, malonic acid, glutaric acid, adipic acid, cyclohexanecarboxylic acid, thiodipropionic acid, dithiodipropionic acid-acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic anhydride, trimellitic anhydride, trifluoroacetic anhydride, and the like; organic phosphorus compounds including phosphates such as mono-, di-, and trimethylphosphate, mono-, di-, and triethyiphosphate, mono-, di-, and triisobutylphosphate, mono-, di-, and tributylphosphate, mono-, di-, and triilaurylphosphate, and the like, including phosphites obtained as a result of the phosphate part of the above-listed substances being changed into phosphite; and also including dialkyldithiophosphate represented by dimethyldithiophosphate; phenols such as phenol, catechol, t-butylcatechol, 2,6-di-t-butylcresol, 2,6-di-t-butylethylphenol, resorcinol, hydroquinone, phloroglucin, pyrogallol, cresol, ethylphenol, butylphenol, nonylphenol, hydroxyphenylacetic acid, hydroxyphenylpropionic acid, amide hydroxyphenylacetate, methyl hydroxyphenylacetate, ethyl hydroxyphenylacetate, hydroxyphenetyl alcohol, hydroxyphenetyl amine, hydroxybenzaldehyde, phenylphenol, bisphenol A, 2,2'-methylene-bis (4-methyl-6-t-butylphenol), bisphenol F, bisphenol S, α-naphthol, β-naphthol, aminophenol, chlorophenol, 2,4,6-trichlorophenol, and the like; sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulphanilic acid, 4B-acid, diaminostilbenesulfonic acid, biphenylsulfonic acid, α-naphthalenesulfonic acid, β-naphthalenesulfonic acid, peri acid, Laurent's acid, phenyl J acid, and the like; etc. A plurality of these may be used in combination. Preferable examples of the acid and acidic anhydride are organic carboxylic acids such as formic acid, acetic acid, peracetic acid, thioacetic acid, oxalic acid, tartaric acid, propionic acid, butyric acid, succinic acid, valeric acid, capronic acid, caprylic acid, naphthenic acid, methylmercaptopropionate, malonic acid, glutaric acid, adipic acid, cyclohexanecarboxylic acid, thiodipropionic acid, dithiodipropionic acid-acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic anhydride, trimellitic anhydride, trifluoroacetic anhydride, and the like. More preferable examples are acidic anhydrides such as acetic anhydride, propionic anhydride, butyric anhydride, succinic anhydride, maleic anhydride, benzoic anhydride, phthalic anhydride, pyromellitic anhydride, trimellitic anhydride, trifluoroacetic anhydride, and the like. Acetic anhydrides are most preferable. The amount of these materials with respect to the total amount of the reaction solution is usually in the range of 0.001% by mass to 10% by mass, and preferably in the range of 0.01% by mass to 5% by mass. When the amount is less than 0.001% by mass, generation of a polymer is conspicuous and the reaction yield is decreased. When the amount exceeds 10% by mass, the yield may be significantly decreased. Specific examples of the ammonium salt include ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate, ammonium hydroxide, and the like. Ammonium nitrate, ammonium sulfate, and ammonium chloride are more preferable. Ammonium nitrate is most preferable.

For a composition for an optical material according to the present invention, the episulfide compound represented by formula (2) is preferable usable as a polymerizable compound. Specific examples of the episulfide compound represented by formula (2) include episulfides such as bis(β-epithiopropyl)sulfide, bis(β-epithiopropyl)disulfide, bis(β-epithiopropyl)methane, 1,2-bis(β-epithiopropylthio)ethane, 1,3-bis(β-epithiopropylthio)propane, 1,4-bis(β-epithiopropylthio)butane, and the like. The episulfide compounds represented by formula (2) may be used independently or as a mixture of two or more thereof.

Among these, bis(β-epithiopropyl)sulfide (n=0 in formula (2)) and bis((3-epithiopropyl)disulfide (m=0, n=1 in formula (2)) are more preferable. Bis((3-epithiopropyl)sulfide (n=0 in formula (2)) is most preferable.

The composition for an optical material according to the present invention may contain a polythiol compound as a polymerizable compound in order to improve the color tone, during heating, of the resin to be obtained. The content of the polythiol compound is, where the total amount of the composition for an optical material is 100% by mass, usually 1 to 25% by mass, preferably 2 to 25% by mass, and especially preferably 5 to 20% by mass. When the content of the polythiol compound is less than 1% by mass, the lens may be colored yellow during molding. When the content of the polythiol compound exceeds 25%, the heat resistance may be decreased. The polythiol compounds usable in the present invention may be used independently or as a mixture of two or more thereof.

Specific examples thereof include methanediol, methanetriol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptoethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycolbis(2-mercaptoacetate), ethyleneglycolbis(3-mercaptopropionate), diethyleneglycolbis(2-mercaptoacetate), diethyleneglycolbis(3-mercaptopropionate), 1,4-buthanediolbis(2-mercaptoacetate), 1,4-buthanediolbis(3-mercaptopropionate), trimethylolpropanetristhioglycolate, trimethylolpropanetrismercaptopropionate, pentaerythritoltetrakisthioglycolate, pentaerythritoltetrakismercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenediol, 1,1,3,3-tetrakis(mercaptomethylthio)propane, and the like.

Specific preferable examples among these are bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritoltetrakismercaptopropionate, pentaerythritoltetrakisthioglycolate, trimethylolpropanetristhioglycolate, and trimethylolpropanetrismercaptopropionate. More preferable examples are bis(2-mercaptoethyl)sulfide, 2,5-bis(2-mercaptomethyl)-1,4-dithiane, 4-mercaptomethyl-1,8-dimercapto-3,6-dithiaoctane, 1,3-bis(mercaptomethyl)benzene, pentaerythritoltetrakismercaptopropionate, and pentaerythritoltetrakisthioglycolate. Most preferable examples are bis(2-mercaptoethyl)sulfide, 2,5-dimercaptomethyl-1,4-dithiane, and 4-mercaptomethyl-1,8-dimercapto-3,6-dithiaoctane.

The composition for an optical material according to the present invention may contain a polyisocyanate compound as a polymerizable compound in order to improve the strength of the resin to be obtained. The content of the polyisocyanate compound is, where the total amount of the composition for an optical material is 100% by mass, usually 1 to 25% by mass, preferably 2 to 25% by mass, and especially preferably 5 to 20% by mass. When the content of the polyisocyanate compound is less than 1% by mass, the strength may be decreased. When the content of the polyisocyanate compound exceeds 25%, the color tone may be decreased. The polyisocyanate compounds usable in the present invention may be used independently or as a mixture of two or more thereof Specific examples thereof include diethylenediisocyanate, tetramethylenediisocyanate, hexamethylenediisocyanate, trimethylhexamethylenediisocyanate, cyclohexanediisocyanate, 1,3-bis(isocyanatemethyl)cyclohexane, 1,4-bis(isocyanatemethyl)cyclohexane, isophoronediisocyanate, 2,6-bis(isocyanatemethyl)decahydronaphthalene, Lysinetriisocyanate, tolylenediisocyanate, o-tolidinediisocyanate, diphenylmethanediisocyanate, diphenyletherdiisocyanate, 3-(2'-isocyanatecyclohexyl)propylisocyanate, isopropylidenebis(cyclohexylisocyanate), 2,2'-bis(4-isocyanatephenyl)propane, triphenylmethanetriisocyanate, bis(diisocyanatetolyl)phenylmethane, 4,4',4"-triisocyanate-2,5-dimethoxyphenylamine, 3,3'-dimethoxybenzine-4,4'-diisocyanate, 1,3-phenylenediisocyanate, 1,4-phenylenediisocyanate, 4,4'-diisocyanatebiphenyl, 4,4'-diisocyanate3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylenediisocyanate, p-xylylenediisocyanate, m-tetramethylxylylenediisocyanate, p-tetramethylxylylenediisocyanate, 1,3-bis(2-isocyanate-2-propyl)benzene, 2,6-bis(isocyanatemethyl)naphthalene, 1,5-naphthalenediisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl isocyanate, thiodipropyldiisocyanate, thiodihexyldiisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyldiisocyanate, dithiodipropyldiisocyanate, and the like.

The polyisocyanate compounds usable in the present invention are not limited to the above, and these may be used independently or as a mixture of two or more thereof Specific preferable examples among these are isophoronediisocyanate, tolylenediisocyanate, diphenylmethanediisocyanate, hexamethylenediisocyanate, m-xylylenediisocyanate, p-xylylenediisocyanate, m-tetramethylxylylenediisocyanate, p-tetramethylxylylenediisocyanate, 1,3-bis(isocyanatemethyl)cyclohexane, 1,4-bis(isocyanatemethyl)cyclohexane, bis(isocyanatemethyl)norbornene, and 2,5-diisocyanatemethyl-1,4-dithiane. At least one compound selected from these is preferably usable. Among these, isophoronediisocyanate, tolylenediisocyanate, diphenylmethanediisocyanate, hexamethylenediisocyanate, 1,3-bis(isocyanatemethyl)cyclohexane, and m-xylylenediisocyanate are more preferable. Isophoronediisocyanate, m-xylylenediisocyanate, and 1,3-bis(isocyanatemethyl)cyclohexane are most preferable.

The ratio of the SH groups in the polythiol compound with respect to the NCO groups in the polyisocyanate compound, namely, [number of SH groups in the polythiol compound/number of NCO groups in the polyisocyanate compound] (SH groups/NCO groups), is preferably 1.0 to 2.5, more preferably 1.25 to 2.25, and still more preferably 1.5 to 2.0 When the ratio is lower than 1.0, the lens may be colored yellow during molding. When the ratio exceeds 2.5, the heat resistance may be decreased.

The composition for an optical material according to the present invention may contain sulfur as a polymerizable compound in order to improve the refractive index of the resin to be obtained. The content of sulfur is, where the total amount of the composition for an optical material is 100% by mass, usually 0.1 to 15% by mass, preferably 0.2 to 10% by mass, and especially preferably 0.3 to 5% by mass.

In the present invention, sulfur may be used in any form. Sulfur is specifically available as powdered sulfur, colloidal sulfur, precipitated sulfur, crystalline sulfur, sublimed sulfur, or the like. Powdered sulfur having microscopic particles is preferable.

Sulfur used in the present invention may be produced by any method. Methods for producing sulfur include a method of subliming and purifying native sulfur ore, a method of mining sulfur buried underground by a melting method, a method of recovering sulfur from hydrogen sulfide obtained from a desulfurization process of petroleum or natural gas, and the like. Any method is usable.

Sulfur used in the present invention preferably has a particle diameter smaller than 10 mesh; namely, it is preferable that the particles of sulfur are finer than 10 mesh. When the particle diameter of sulfur is larger than 10 mesh, sulfur is not likely to be fully dissolved. Therefore, an undesirable reaction or the like occurs in the first step and a flaw may be caused. The particle diameter of sulfur is more preferably smaller than 30 mesh, and most preferably smaller than 60 mesh.

Sulfur used in the present invention has a purity of preferably 98% or higher, more preferably 99.0% or higher, still more preferably 99.5% or higher, and most preferably 99.9% or higher. When the purity of sulfur is 98% or higher, the color tone of the optical material to be obtained is improved as compared with when the purity of sulfur is lower than 98%.

For producing an optical material by polymerizing and curing a composition for an optical material according to the present invention, it is preferable to add a polymerization catalyst. Examples of usable polymerization catalysts include amine, phosphine, onium salt, and the like. Especially, onium salt is preferable. Preferable examples of the onium salt are quaternary ammonium salt, quaternary phosphonium salt, tertiary sulfonium salt, and secondary iodonium salt. Among these, quaternary ammonium salt and quaternary phosphonium salt, which are highly compatible with the composition for an optical material, are more preferable. Quaternary phosphonium salt is still more preferable. Further preferable example of polymerization catalysts include quaternary ammonium salts such as tetra-n-butylammoniumbromide, triethylbenzylammoniumchloride, cetyldimethylbenzylammoniumchloride, 1-n-dodecylpyridiniumchloride, and the like; and quaternary phosphonium salts such as tetra-n-butylphosphoniumbromide, tetraphenylphosphoniumbromide, and the like. Among these, tetra-n-butylammoniumbromide, triethylbenzylammoniumchloride, and tetra-n-butylphosphoniumbromide are still more preferable.

The amount of the polymerization catalyst depends on the components of the composition, the mixing ratio, and the polymerization and curing method, and thus is not uniquely defined. The amount of the polymerization catalyst is, where the total amount of the composition for an optical material is 100% by mass, usually 0.0001% by mass to 10% by mass, preferably 0.001% by mass to 5% by mass, more preferably 0.01% by mass to 1% by mass, and most preferably 0.01% by mass to 0.5% by mass. When the amount of the polymerization catalyst is larger than 10% by mass, the polymerization may advance rapidly. When the amount of the polymerization catalyst is smaller than 0.0001% by mass, the composition for an optical material is not fully cured, which may result in an insufficient heat resistance.

For producing an optical material by use of a method according to the present invention, an additive such as an ultraviolet absorber, a bluing agent, a pigment or the like may be added to the composition for an optical material in order to improve the usability of the optical material to be obtained, needless to say.

Preferable examples of the ultraviolet absorber include benzotriazole compounds. Especially preferable compounds are 2-(2-hydroxy-5-methylphenyl)-2H-benzotriazole, 5-chloro-2-(3,5-di-tert-butyl-2-hydroxyphenyl)-2H-benzotriazole, 2-(2-hydroxy-4-octylphenyl)-2H-benzotriazole, 2-(2-hydroxy-4-methoxyphenyl)-2H-benzotriazole, 2-(2-hydroxy-4-ethoxyphenyl)-2H-benzotriazole, 2-(2-hydroxy-4-butoxyphenyl)-2H-benzotriazole, 2-(2-hydroxy-4-octyloxyphenyl)-2H-benzotriazole, and 2-(2-hydroxy-5-t-octylphenyl)-2H-benzotriazole.

The amount of such an ultraviolet absorber is, where the total amount of the composition for an optical material is 100% by mass, usually 0.01 to 5% by mass.

For polymerizing and thus curing the composition for an optical material, an polymerization adjusting agent may be added as necessary in order to, for example, extend the pot life or disperse the polymerization heat. Examples of the polymerization adjusting agent include halides of groups XIII to XVI in the long periodic table. Preferable compounds among these are halides of silicon, germanium, tin and antimony. More preferable compounds are chlorides of germanium, tin and antimony containing an alkyl group. Still more preferable compounds are dibutyltindichloride, butyltintrichloride, dioctyltindichloride, octyltintrichloride, dibutyldichlorogermanium, butyltrichlorogermanium, diphenyldichlorogermanium, phenyltrichlorogermanium, and triphenylantimonydichloride. Dibutyltindichloride is most preferable. The polymerization adjusting agents may be used independently or as a mixture of two or more thereof.

The amount of the polymerization adjusting agent is, where the total amount of the composition for an optical material is 100% by mass, usually 0.0001 to 5.0% by mass, preferably 0.0005 to 3.0% by mass, and more preferably 0.001 to 2.0% by mass. When the amount of the polymerization adjusting agent is smaller than 0.0001% by mass, a sufficient pot life is not guaranteed for the composition for an optical material to be obtained. When the amount of the polymerization adjusting agent is larger than 5.0% by mass, the composition for an optical material is not sufficiently cured, and the heat resistance of the optical material to be obtained may be decreased.

The composition for an optical material thus obtained is injected into a mold or the like and polymerized to be formed into an optical material.

For injecting the composition for an optical material according to the present invention, it is preferable to remove impurities by use of a filter or the like having a pore diameter of about 0.1 to 5 μm. This is preferable from the point of view of improving the quality of the optical material.

The composition for an optical material according to the present invention is usually polymerized as follows. The curing time is usually 1 to 100 hours, and the curing temperature is usually −10° C. to 140° C. The polymerization is performed by a step of maintaining the composition for an optical material at a predetermined polymerization temperature for a predetermined time duration, a step of raising the temperature in the range of 0.1° C. to 100° C./h, a step of lowering the temperature in the range of 0.1° C. to 100° C./h, or a combination of these steps.

It is preferable to, after the curing is finished, anneal the obtained optical material at a temperature of 50 to 150° C. for about 10 minutes to 5 hours. This is preferable to remove distortion of the optical material according to the present invention. The obtained optical material may be subjected to a surface treatment as necessary such as, for example, dying, hard coating, impact resistance coating, reflection prevention, anti-fogging or the like.

The optical material according to the present invention is preferably used as a lens.

EXAMPLES

Hereinafter, the present invention will be described by way of examples and comparative examples. The present invention is not limited to the following examples.
1. Stability An episulfide compound, which is a main component of the composition for an optical material (i.e., episulfide compound as a polymerizable compound), was traced regarding the change of the purity at 60° C. for 1 week in a nitrogen atmosphere by use of GPC analysis. A sample which had the purity decreased by less than 5% was evaluated as A, a sample which had the purity decreased by 5% or greater and less than 10% was evaluated as B, and a sample which had the purity decreased by 10% or greater was evaluated as C. A and B pass the test.
2. Evaluation on Light Resistance (Color Tone Measurement)
(1) Measurement of the Initial Value A flat plate having a thickness of 3.0 mm was produced by a method described in the examples, and the YI value was measured by colorimeter JS-555 produced by Color Techno System Corporation. The obtained value is labeled as p.
(2) Measurement of Color Tone Change by Light After the initial value was measured, the flat plate was irradiated with carbon arc combustion light for 60 hours. After this, the YI value was measured. The obtained value is labeled as q.

The value of (q−p)/p was calculated. A sample with this value of less than 1.0 was evaluated as A. A sample with this value of 1.0 or greater and less than 2.0 was evaluated as B. A sample with this value of 2.0 or greater was evaluated as C. A and B pass the test.
3. Releasability A −4D lens was produced by a method described in the examples, and the releasability of the polymerized and cured lens from the mold was evaluated. A sample which was released easily was evaluated as A. A sample which was released was evaluated as B. A sample which was not released easily was evaluated as C. A and B pass the test.

Example 1

185 g (2.0 mol) of epichlorhydrin, 30 g of water, 5 g of methanol, and 1.5 g of 32% aqueous solution of sodium hydroxide were put. While these substances were stirred, 35 g (1.0 mol) of hydrogen sulfide was blown to the substances with the liquid temperature being kept at 5 to 15° C. As a result, 210 g (0.96 mol) of bis(3-chloro-2-hydroxypropyl)sulfide was obtained.

100 g of water was put, and then 120 g of 32% aqueous solution of sodium hydroxide was dripped thereto while the temperature thereof was kept at 0 to 10° C. Then, 300 g of methylisobutylketone was put for extraction. The obtained organic layer was washed with 1% acetic acid and then washed with water, and the solvent was removed by distillation. Then, the resultant substance was purified by a column to obtain 105 g (0.58 mol) of 1-chloro-2-hydroxy-6,7-epoxy-4-thiaheptane.

Then, 750 ml of toluene, 750 ml of methanol, 0.2 g of acetic anhydride, and 177 g of thiourea were put to cause a reaction at 40° C. for 10 hours. Toluene was used for extraction. The obtained organic layer was washed with 10% sulfuric acid and then washed with water, and the solvent was removed by distillation. Then, the resultant substance was purified by a column to obtain 40 g (0.20 mol) of 1-mercapto-2-hydroxy-6,7-epithio-4-thiaheptane represented by the following formula.

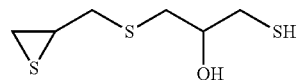

$^1$H-NMR (CDCl$_3$): 1.5 ppm (1H), 2.0 ppm (1H), 2.2-2.7 ppm (9H), 3.8 ppm (1H)
$^{13}$C-NMR (CDCl$_3$): 25 ppm, 33 ppm (2C), 39 ppm, 45 ppm, 78 ppm Example 2

190 g (2.1 mol) of epichlorhydrin, 500 ml of methanol, and 1.0 g of calcium hydroxide were put. While these substances were stirred, 75 g (2.2 mol) of hydrogen sulfide was blown to the substances with the liquid temperature being kept at 0 to 5° C. As a result, chloromercaptopropanol was obtained. Then, 1000 ml of water and 168 g of sodium hydrogen carbonate were put, and 254 g of iodine was put with the liquid temperature being kept at 5 to 10° C. After the reaction was performed at 10° C. for 12 hours, filtration and drying were performed. Thus, bis(3-chloro-2-hydroxypropyl)disulfide was obtained.

100 g of water was put, and then 120 g of 32% aqueous solution of sodium hydroxide was dripped thereto while the temperature thereof was kept at 0 to 10° C. Then, 300 g of methylisobutylketone was put for extraction. The obtained organic layer was washed with 1% acetic acid and then washed with water, and the solvent was removed by distillation. Then, the resultant substance was purified by a column to obtain 20 g (0.09 mol) of 1-chloro-2-hydroxy-7,8-epoxy-4,5-dithiaoctane.

Then, 750 ml of toluene, 750 ml of methanol, 0.2 g of acetic anhydride, and 177 g of thiourea were put to cause a reaction at 40° C. for 10 hours. Toluene was used for extraction. The obtained organic layer was washed with 10% sulfuric acid and then washed with water, and the solvent was removed by distillation. Then, the resultant substance was purified by a column to obtain 9.0 g (0.04 mol) of 1-mercapto-2-hydroxy-7,8-epithio-4,5-dithiaoctane represented by the following formula.

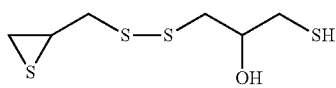 [SMILES: OC(CS)CSSCC1CS1]

$^1$H-NMR (CDCl$_3$): 1.5 ppm (1H), 2.0 ppm (1H), 2.2-3.0 ppm (9H), 3.8 ppm (1H)
$^{13}$C-NMR (CDCl$_3$): 24 ppm, 32 ppm (2C), 41 ppm, 46 ppm, 77 ppm Examples 3-8

To bis(β-epithiopropyl)sulfide (hereinafter, referred to as "compound a") as a polymerizable compound, 1-mercapto-2-hydroxy-6,7-epithio-4-thiaheptane (hereinafter, referred to as "compound b") prepared in embodiment 1 and represented by formula (1) was added in an amount shown in Table 1. The stability was evaluated. The results are shown in Table 1.

Examples 9-14

To bis(β-epithiopropyl)disulfide (hereinafter, referred to as "compound c") as a polymerizable compound, 1-mercapto-2-hydroxy-7,8-epithio-4,5-dithiaoctane (hereinafter, referred to as "compound d") prepared in embodiment 2 and represented by formula (1) was added in an amount shown in Table 1. The stability was evaluated. The results are shown in Table 1.

Comparative Example 1

The stability of only compound a was evaluated. The results are shown in Table 1.

Comparative Example 2

The stability of only compound c was evaluated. The results are shown in Table 1.

TABLE 1

| Example | Main component | Component and amount (% by mass) | Stability |
|---|---|---|---|
| Example 3 | Compound a | Compound b 0.001 | B |
| Example 4 | Compound a | Compound b 0.005 | B |
| Example 5 | Compound a | Compound b 0.01 | A |
| Example 6 | Compound a | Compound b 1.0 | A |
| Example 7 | Compound a | Compound b 3.0 | A |
| Example 8 | Compound a | Compound b 5.0 | A |
| Comparative example 1 | Compound a | None | C |
| Example 9 | Compound c | Compound d 0.001 | B |
| Example 10 | Compound c | Compound d 0.005 | B |
| Example 11 | Compound c | Compound d 0.01 | A |
| Example 12 | Compound c | Compound d 1.0 | A |
| Example 13 | Compound c | Compound d 3.0 | A |

TABLE 1-continued

| Example | Main component | Component and amount (% by mass) | Stability |
|---|---|---|---|
| Example 14 | Compound c | Compound d 5.0 | A |
| Comparative example 2 | Compound c | None | C |

Examples 15-20

Compound a and compound b were mixed at a ratio shown in Table 2. 1.0% by mass of 2-(2-hydroxy-5-t-octylphenyl)-2H-benzotriazole as an ultraviolet absorber and 0.05% by mass of tetra-n-butylphosphoniumbromide as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C. for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

Comparative Example 3

To compound a, 1.0% by mass of 2-(2-hydroxy-5-t-octylphenyl)-2H-benzotriazole as an ultraviolet absorber and 0.05% by mass of tetra-n-butylphosphoniumbromide as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C. for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

Comparative examples 4 and 5

Compound a and 1-chloro-2-hydroxy-6,7-epoxy-4-thiaheptane represented by the following formula (hereinafter, referred to as "compound e") were mixed at a ratio shown in Table 2. 1.0% by mass of 2-(2-hydroxy-5-t-octylphenyl)-2H-benzotriazole as an ultraviolet absorber and 0.05% by mass of tetra-n-butylphosphoniumbromide as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C.

for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

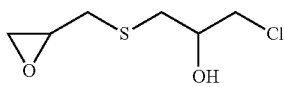

Examples 21-26

Compound c and compound d were mixed at a ratio shown in Table 2. 1.0% by mass of 2-(2-hydroxy-5-t-octylphenyl)-2H-benzotriazole as an ultraviolet absorber and 0.5% by mass of N,N-dimethylcyclohexylamine as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C. for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

Comparative Example 6

To compound c, 1.0% by mass of 2-(2-hydroxy-5-t-octylphenyl)-2H-benzotriazole as an ultraviolet absorber and 0.5% by mass of N,N-dimethylcyclohexylamine as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C. for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

Comparative examples 7 and 8

Compound c and 1-chloro-2-hydroxy-7,8-epoxy-4,5-dithiaoctane represented by the following formula (hereinafter, referred to as "compound f") were mixed at a ratio shown in Table 2. 1.0% by mass of 2-(2-hydroxy-5-t-octylphenyl)-2H-benzotriazole as an ultraviolet absorber and 0.5% by mass of N,N-dimethylcyclohexylamine as a polymerization catalyst were added, and the substances were well mixed at 20° C. to be uniform. Then, the obtained substance was deaerated at a vacuum degree of 1.3 kPa, and injected to a mold formed of two glass plates and a tape (for a flat plate having a thickness of 3.0 mm and a −4D lens). The substance was heated at 30° C. for 10 hours, had the temperature raised to 100° C. over 10 hours at a constant rate, and then was heated at 100° C. for 1 hour to be polymerized and cured. After being cooled, the substance was released from the mold and annealed at 110° C. for 60 minutes. Thus, a molded plate (a flat plate having a thickness of 3.0 mm and a −4D lens) was obtained. The light resistance of the flat plate was evaluated (color tone measurement), and the releasability of the −4D lens was evaluated. The results are shown in Table 2.

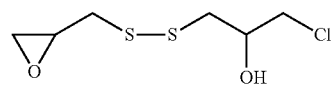 [SMILES: OC(CCl)CSSCC1CO1]

TABLE 2

| Example | Main component | Component and amount (% by mass) | Light resistance | Releasability |
|---|---|---|---|---|
| Example 15 | Compound a | Compound b 0.001 | B | A |
| Example 16 | Compound a | Compound b 0.005 | A | A |
| Example 17 | Compound a | Compound b 0.01 | A | A |
| Example 18 | Compound a | Compound b 1.0 | A | A |
| Example 19 | Compound a | Compound b 3.0 | A | B |
| Example 20 | Compound a | Compound b 5.0 | A | B |
| Comparative example 3 | Compound a | None | C | A |
| Comparative example 4 | Compound a | Compound e 0.01 | C | A |
| Comparative example 5 | Compound a | Compound e 1.0 | C | C |
| Example 21 | Compound c | Compound d 0.001 | B | A |
| Example 22 | Compound c | Compound d 0.005 | B | A |
| Example 23 | Compound c | Compound d 0.01 | A | A |
| Example 24 | Compound c | Compound d 1.0 | A | A |
| Example 25 | Compound c | Compound d 3.0 | A | B |
| Example 26 | Compound c | Compound d 5.0 | A | B |
| Comparative example 6 | Compound c | None | C | A |
| Comparative example 7 | Compound c | Compound f 0.01 | C | A |
| Comparative example 8 | Compound c | Compound f 1.0 | C | C |

The invention claimed is:

1. An episulfide compound represented by formula (1) below:

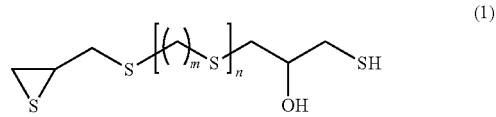

(where m represents an integer of 0 to 4, and n represents an integer of 0 to 2).

2. A composition for an optical material, comprising the episulfide compound according to claim 1, and a polymerizable compound.

3. The composition for an optical material according to claim 2, wherein the episulfide compound is contained at a content of 0.001 to 5.0% by mass.

4. The composition for an optical material according to claim 2, wherein the polymerizable compound is contained at a content of 95.0 to 99.999% by mass.

5. The composition for an optical material according to claim 2, wherein an episulfide compound represented by formula (2) below is contained as the polymerizable compound:

(2)

(where m represents an integer of 0 to 4, and n represents an integer of 0 to 2).

6. The composition for an optical material according to claim 5, wherein the episulfide compound represented by formula (2) is contained at a content of 40 to 99.999% by mass.

7. A method for producing an optical material, comprising adding a polymerization catalyst to the composition for an optical material according to claim 2 at a content of 0.0001% by mass to 10% by mass with respect to the total amount of the composition for an optical material, thereby causing polymerization and curing.

8. An optical material produced by the method according to claim 7.

9. An optical lens, comprising the optical material according to claim 8.

10. A method for producing the episulfide compound represented by formula (1) below according to claim 1:

(1)

(where m represents an integer of 0 to 4, and n represents an integer of 0 to 2), the method comprising the steps of:
reacting hydrogen sulfide or a polythiol compound with an epihalohydrin compound to obtain a compound represented by formula (3) below;
reacting the obtained compound represented by formula (3) with an alkali to proceed with a dehydrohalogenation reaction to obtain a compound represented by formula (4) below; and
reacting the obtained compound represented by formula (4) with a thiating agent to obtain the compound represented by formula (1) above:

(3)

(where X represents a halogen atom, m represents an integer of 0 to 4, and n represents an integer of 0 to 2);

(4)

(where X represents a halogen atom, m represents an integer of 0 to 4, and n represents an integer of 0 to 2).

* * * * *